(12) United States Patent
Himmelsbach et al.

(10) Patent No.: US 6,506,957 B1
(45) Date of Patent: Jan. 14, 2003

(54) SELF-ADHESIVE SHAPED BODY

(75) Inventors: Peter Himmelsbach, Buxtehude (DE); Thorsten Herzberg, Hamburg (DE)

(73) Assignee: Beiersdorf AG, Hamburg (DE)

( * ) Notice: Subject to any disclaimer, the term of this patent is extended or adjusted under 35 U.S.C. 154(b) by 133 days.

(21) Appl. No.: 09/620,383

(22) Filed: Jul. 20, 2000

(30) Foreign Application Priority Data

Aug. 12, 1999 (DE) .......................................... 199 38 322

(51) Int. Cl.[7] ................................................. A61F 13/00
(52) U.S. Cl. ............................. 602/41; 602/42; 602/52; 602/54
(58) Field of Search ................................ 602/41–47, 6, 602/20, 21, 23–27, 36, 52–54, 58; 442/181, 304

(56) References Cited

U.S. PATENT DOCUMENTS

| | | | |
|---|---|---|---|
| 3,934,583 A | 1/1976 | Hillingshead et al. | ...... 128/165 |
| 5,306,229 A | 4/1994 | Brandt et al. | ............... 602/26 |

FOREIGN PATENT DOCUMENTS

| | | | | |
|---|---|---|---|---|
| DE | 86257986 U1 | 9/1986 | ........... | A61F/13/10 |
| DE | 41 01 965 A1 | 7/1992 | ........... | A61F/13/06 |
| DE | 42 37 389 A1 | 5/1994 | ........... | A61F/13/06 |
| DE | 42 38 610 A1 | 5/1994 | ........... | A61F/13/00 |
| DE | 296 18 426 U1 | 4/1997 | ........... | A61F/13/00 |
| DE | 196 20 107 A1 | 11/1997 | ........... | C09J/7/04 |
| DE | 196 20 109 A1 | 11/1997 | ........... | C09J/7/04 |
| DE | 197 55 222 A1 | 6/1999 | ........... | C09J/7/02 |
| DE | 197 51 873 A1 | 8/1999 | ........... | C09J/7/02 |
| EP | 0 027 172 A1 | 4/1981 | ........... | A61F/13/00 |
| WO | 86/04811 A1 | 8/1986 | ........... | A61F/13/10 |
| WO | 96/11236 | * 4/1996 | ........... | 53/2 |

OTHER PUBLICATIONS

Patent Abstracts of Japan, Publication No. 06022999, Publication Date Feb. 01, 1994, Applicant Saitama Daiichi Seiyaku KK.

Patent Abstracts of Japan, Publication No. 04305522, Publication Date Oct. 28, 1992, Applicant Sekisui Chem Co. Ltd.

* cited by examiner

*Primary Examiner*—Michael A. Brown
*Assistant Examiner*—Lalita Hamilton
(74) *Attorney, Agent, or Firm*—Norris McLaughlin & Marcus

(57) ABSTRACT

Self-adhesive shaped body which is adapted to the anatomy, has a proprioceptive effect and is intended for medical purposes, having a bond strength of from 1 N/cm to 25 N/cm, an extensibility of more than 10%, a thickness of more than 0.5 mm and a resilience of more than 50% for a tensile stress of 5 N/cm$^2$.

11 Claims, 2 Drawing Sheets

SELF-ADHESIVE SHAPED BODY

The invention relates to a self-adhesive shaped body, also referred to as a cushioning pad, and possessing high resilience, for orthopaedic purposes, especially for prophylaxis, postoperative treatment and therapy, especially for more rapidly reestablishing the function of injured joints, such as knee, ankle, shoulder, elbow and/or wrist joints.

BACKGROUND OF THE INVENTION

The bandaging of joints, for example following injury or in the case of degenerative disorders, is a known method of orthopaedic treatment. The spectrum ranges from simple winding with more or less elastic bandages, through ready-made bandages in a wide variety of embodiments, and on to braces and splints of complex construction.

Additionally, the functional dressing technique, known as taping, is a treatment method for the prophylaxis and therapy of injuries, diseases and alterations on the locomotor apparatus. The purpose of taping is to mimic the capsular ligament structures and so achieve selective support and stabilization.

The actual tape dressing is applied in strips comprising preferably inelastic self-adhesive bands, known as straps, or in conjunction with self-adhesive bands having short-pull elasticity. It protects, supports and relieves vulnerable, damaged or disrupted parts of a functional unit. It permits selective loading within the pain-free sphere of movement, but prevents extreme or painful movements.

The application of such dressings, however, requires expert skill and experience and, consequently, cannot in general be performed by non-experts without taping experience.

A large number of bandages are known which aim to reestablish the function of injured joints.

EP 0 027 172 A1 describes a bandage in tube form for supporting and/or compressing knee, ankle, elbow and/or wrist joints. An adhesive coating of the bandage is not described.

An epicondylitis bandage is disclosed by EP 0 250 409 A1. An epicondylitis bandage of this kind consists essentially of a tube section comprising elastic material, the tensile stress in the peripheral direction being alterable by way of a tensioning strap which extends essentially in the peripheral direction and has a closure. The bandage is not self-adhesive.

DE 41 01 965 A1 discloses a joint bandage comprising elastic bandage material with a soft and a hard component and at least one friction core. Self-adhesive properties are not described. The joint bandage permits targeted transverse frictional massage for the more rapid reestablishment of the functions of injured joints such as knee, ankle, elbow, shoulder and wrist joints and has an insert which in the applied state acts on the joint and is designed as a compression cushioning pad, this pad having a form determined by the bone projections and tendon insertions of the joint and, as a shaped body, being formed from a soft or soft-elastic material in which at least one friction core comprising a hard or incompressible material is arranged and is fixed in its position in the material of the shaped body.

DE 42 37 389 A1 describes a knee joint bandage having corresponding anatomical forms. Self-adhesive properties are not described. The bandage for overcharge phenomena, femoropatellar pain syndromes and the patella tip syndrome, comprising an elastic bandage material in tube form with an encircling insert comprising a wavy knit, possesses, in the front part of the bandage, a cushioning pad which is situated in the region over the patella with the bandage applied, is upwardly open and leaves the quadricipital tendon free, and, in the rear part of the bandage, one or two cushioning pads which are arranged at a distance from one another and which act on the insert of the ischiocrural musculature.

It is an object of the invention to provide an anatomically designed shaped body for orthopaedic purposes which on the basis of the self-adhesive properties adheres to the skin or to an underlaid material, whereby owing to the high resilience of the shaped body when correctly applied a massage effect is established which leads to a more rapid reestablishment of the function of injured joints, such as knee, ankle, shoulder, elbow and/or wrist joints. In addition, the shaped body ought to improve the proprioceptive effect.

SUMMARY OF THE INVENTION

This object is achieved by means of a self-adhesive shaped body which is adapted to the anatomy and has a proprioceptive effect and is intended for medical purposes, as is described in the main claim. The subsidiary claims depict advantageous embodiments of the invention.

Accordingly, the invention provides a self-adhesive shaped body which is adapted to the anatomy, has a proprioceptive effect and is intended for medical purposes, having a bond strength of from 1 N/cm to 25 N/cm, an extensibility of more than 10%, a thickness of more than 0.5 mm and a resilience of more than 50% for a tensile stress of 5 N/cm$^2$.

The shaped body of the invention is based on a composition which is designed so as to be self-adhesive by virtue of appropriate process steps or formulation with tackifiers.

To significant extents the body comprises an elastic polymer selected from the group consisting of polyurethane, polyester, polyether, polyepoxide, polyolefin and/or an elastic polymer based on a natural or synthetic rubber.

The technical properties of the shaped body may be adjusted depending on the field of use. In some cases, strongly adhering systems, or else less pressure-sensitive adhesive systems, are required for the shaped body. To this end, appropriate additives such as tackifier resins, plasticizers, stabilizers and other auxiliaries may be added to the respective system.

Advantageous embodiments exhibit a bond strength of from 1.5 to 22 N/cm, with particular preference from 1.5 to 18 N/cm. In one specific embodiment for the knee the bond strength is 14.5 N/cm. In another specific embodiment, for the elbow, the bond strength is 16.0 N/cm.

In one particularly preferred embodiment, the composition used to produce the shaped body is a thermoplastic hot-melt composition. The softening point of the thermoplastic hot-melt composition should be greater than 50° C., since the application temperature in the course of production is generally at least 70° C., preferably between 90° C. and 190° C. If desired, postcrosslinking by means of UV or electron beam irradiation may be appropriate. This depends on the chosen structure of the parent polymer or its additives.

The blending of block copolymers based on SEPS and SEBS for producing a shaped body of the invention, in particular, is notable for its diverse possibilities for variation. For particularly strongly adhering systems, the cohesive adhesive composition is based preferably on diblock (A-B)

or triblock (A-B-A) block copolymers and/or mixtures thereof, preference being given to a diblock copolymer fraction of less than 80% by weight. The hard phase A is ideally polystyrene or its derivatives, and the soft phase B comprises ethylene and propylene and/or butylene or mixtures thereof.

The chain of the phase B may also include fractions of other kinds, such as, for example, isoprene, butadiene or similar substances. However, polystyrene blocks may also be present in the soft phase B, in proportions of up to 20% by weight. The overall styrene content, however, should always be lower than 65% by weight, preferably less than 40% by weight, with particular preference from 3 to 35% by weight. Preference is given to styrene fractions of between 3% by weight and 35% by weight, since a lower styrene fraction makes the adhesive composition more conforming.

In one advantageous embodiment the adhesive composition is composed as indicated below:

| | |
|---|---|
| from 5% by weight to 90% by weight | of block copolymers, |
| from 5% by weight to 80% by weight | of tackifiers such as oils, waxes, resins and/or mixtures thereof, preferably mixtures of resins and oils, |
| less than 60% by weight | of plasticizers, |
| less than 15% by weight | of additives and |
| less than 5% by weight | of stabilizers. |

The aliphatic or aromatic oils, waxes and resins used as tackifiers are preferably hydrocarbon oils, waxes and resins, with the consistency of the oils, such as paraffinic hydrocarbon oils, or of the waxes, such as paraffinic hydrocarbon waxes, accounting for their favourable effect on the adhesion. Plasticizers used are medium- or long-chain fatty acids and/or their esters. These additions serve to establish the adhesion properties and the stability. If desired, further stabilizers and other auxiliaries are employed.

Filling the cohesive adhesive composition with mineral fillers, fibres, or hollow or solid microbeads is possible, so as to give, for example, a body of this kind comprising a hard core and a soft periphery. In use, this may give rise to a deep-down massage.

Advantageous for special applications are core materials having a Shore hardness (A) of less than 90, preferably from 80 to 10, with particular preference from 70 to 20. Römpp gives the following explanations in relation to the Shore hardness (Römpp Lexikon Chemie—Version 1.5, Stuttgart/ New York: Georg Thieme Verlag 1998): According to DIN 53505 (1987-06), in the testing of elastomers and rubber, the Shore hardness corresponds to the resistance to penetration of a cone frustum (A or C) or of a rounded cone (D), as measured by the compression of a spring having defined spring characteristics and as expressed in dimensionless Shore A (C, D) hardness units. In the case of the testing of steel, the Shore rebound hardness is measured in the so-called scleroscope, in which the rebound height of a hammer which falls on the test surface in a vertical tube is measured.

In other embodiments, this core material is not adhesive.

For specific application, furthermore, natural rubber or other synthetic rubber types, such as butyl rubber, chloroprene and silicone rubber, may be used.

For stressed joint regions in particular, stringent requirements are imposed in respect of the adhesion properties. For ideal application, the shaped body should possess a high tack. Furthermore, so that there is no slipping, the pressure-sensitive adhesive composition chosen for producing the shaped body is required to possess high shear strength. The targeted reduction in the glass transition temperature of the pressure-sensitive adhesive composition, as a consequence of the selection of the tackifiers, of the plasticizers and of the polymer molecule size, and of the molecular distribution of the components employed, achieves the necessary bonding, appropriate to its function, with the skin, even at critical points on the human locomotor system, and/or with an underlaid material. Product properties such as tack and shear stability may be quantified readily with the aid of a dynamomechanical frequency measurement. In this case, use is made of a rheometer controlled by shearing stress. The results of this measurement method give information on the physical properties of a substance by taking into account the viscoelastic component. In this instance, at a predetermined temperature, the cohesive adhesive composition is set in oscillation between two plane-parallel plates with variable frequencies and low deformation (linear viscoelastic region). Via a pickup control unit, with computer assistance, the quotient (Q =tan δ) between the loss modulus (G", viscous component) and the storage modulus (G', elastic component) is determined.

$$Q = \tan \delta = G''/G'$$

A high frequency is chosen for the subjective sensing of the tack and a low frequency for the shear strength. A low numerical value denotes low tack and good shear stability.

| Designation | Shear strength low frequency/RT | Tack high frequency/RT |
|---|---|---|
| Pressure-sensitive adhesive composition A | tan δ = 0.12 ± 0.03 | tan δ = 1.0 ± 0.1 |
| Pressure-sensitive adhesive composition B | tan δ = 0.37 ± 0.03 | tan δ = 1.7 ± 0.1 |

In accordance with the invention, to form the shaped body, preference is given to pressure-sensitive adhesive compositions in which the ratio of the viscous component to the elastic component at a frequency of 100 rad/s at 25° C. is greater than 0.4, or to adhesive compositions where the ratio of the viscous component to the elastic component at a frequency of 0.1 rad/s at 25° C. is less than 0.5, preferably between 0.35 and 0.02, with very particular preference between 0.3 and 0.05. The adhesive compositions are also preferably formulated so that at a frequency of 0.1 rad/s they have a dynamic-complex glass transition temperature of less than 25°C., preferably of less than 10°C., with very particular preference from 5° C. to −150°C.

Because of the ratio, chosen ideally in accordance with the invention, the cushioning pads exhibit favourable resilience properties. In one preferred embodiment, with a tensile stress of 5 N/cm, based on the width of the article, a resilience of more than 50%, preferably from 55% to 98%, with particular advantage from 60% to 90%, is obtained. In this way, fatigue of the material, as occurs for example under the load conditions of a sport, is reduced. The high shear strength of the adhesive composition is achieved by means of the cohesive nature of the polymer, especially block copolymer.

A further-reaching improvement in relation to the known prior art can be achieved by providing extensible embodiments of the cushioning pads. In this case, an improvement in the proprioceptive effect is found for long-term application, since cushioning pads of inadequate extensibility do not bond durably and thus have a much-reduced, or absent, proprioceptive effect. The extensibility depends on the corresponding use of the product. In general, extensions of more than 10% are necessary. For one specific embodiment on the knee, the minimum extensibility should be 70%; for another specific embodiment for use on the elbow, it should be 50%.

In one particular embodiment, the shaped body may be dehered by extension; for this purpose, as well, good extensibility of the cushioning pad material is required.

Another particular embodiment of the shaped bodies is doped with releasable substances having a local or systemic action. In one specific case, the shaped body which can be dehered by extension has been treated with an active substance which can be released to the skin.

The shaped bodies may be produced from the melt of the abovementioned composition. A variety of production processes may be suitable in this case, whereby advantages may arise depending on the intended use. Common modes of production are casting, compression moulding, injection moulding, spraying, extrusion, calendering and also punching, embossing, stretching, cutting or a combination thereof.

Figure 1:
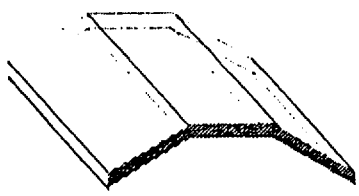
FIG. 1 shows the self-adhesive shaped body of the invention in an extruded flat profile.
Figure 2:
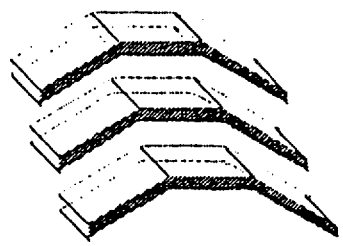
FIG. 2 shows the self-adhesive shaped body of FIG. 1, cut into individual forms.

For flat shaped bodies it is possible to extrude profiles, as shown, for example, by FIG. 1. Subsequently, the extruded profiles may be cut into discs, as shown in FIG. 2. In some cases, cooling is advantageous here prior to cutting.

Figure 3:
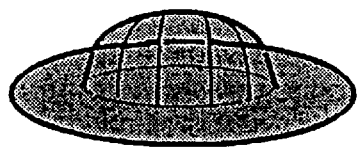
FIG. 3 shows a form of the self-adhesive shaped body of the invention produced by molding.
Figure 4:
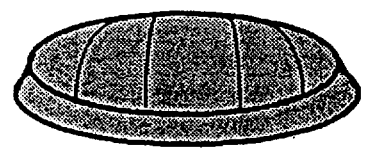
FIG. 4 shows a second form of the self-adhesive shaped body of the invention produced by molding.

A further mode of production is mould casting. Here, the melted composition is introduced into an abhesively treated mould. Advantageously, this can be done under pressure. Following the solidification of the melt, the moulding is removed from the mould and a new occupation can begin. Possible forms of shaped bodies produced in this way are depicted in FIGS. 3 and 4.

For specific anatomical forms, the moulding may also be punched or cut from a spatially limited plate or from a continuous strip.

One continuous process is the screen printing process. In this process, by way of a coating bar, the melt is introduced into depressions and at another point is removed from the depression. This process is normally carried out using auxiliary backings to which the shaped bodies are applied temporarily. This produces stippled surfaces which give a better massage effect.

In specific embodiments of the shaped body, the prior foaming of the adhesive compositions thereof may be advantageous. The adhesive compositions are in this case foamed preferably using inert gases such as nitrogen, carbon dioxide, noble gases, hydrocarbons or air, or mixtures thereof. In some cases, foaming additionally by thermal decomposition of gas-evolving substances, such as azo, carbonate and hydrazide compounds, has proved to be suitable.

The degree of foaming, i.e. the gas content, should be at least about 5% by volume and can range up to about 85% by volume. In practice, levels of from 10% by volume to 75% by volume, preferably 50% by volume, have been found to be appropriate. Operating at relatively high temperatures of approximately 100° C. and with a comparatively high internal pressure produces very open-pored adhesive foam layers which are particularly permeable to air and water vapour. In addition, the at least partly open-pored shaped bodies are able to absorb moisture.

The advantageous property is the excellent conformability even on uneven surfaces owing to the elasticity and plasticity of the foamed shaped body. This advantage is manifested in particular in the case of bone projections (for example, on the ankle joint).

A particularly suitable process for producing the device foamed in accordance with the invention operates in accordance with the foam mix system. In this system, the thermoplastic adhesive composition is reacted with the intended gases such as, for example, nitrogen, air or carbon dioxide in different volume fractions (from about 10% by volume to 80% by volume) in a stator/rotor system under high pressure and at a temperature above the softening point (approximately 120° C.).

While the gas entry pressure is greater than 100 bar, the mixing pressures between gas and thermoplastic in the system are from 40 to 100 bar, preferably from 40 to 70 bar. The pressure-sensitive adhesive foam produced in this way may subsequently pass through a line into the applicator unit. In the applicator unit, commercially customary nozzles, extruder systems or chamber systems are used. By virtue of the foaming of the shaped body and the resultant open pores in the composition, and given the use of an inherently porous backing, the products coated with the device are highly permeable to water vapour and air. The required amount of pressure-sensitive adhesive is considerably reduced without adversely affecting the mode of action and properties.

Figure 5:
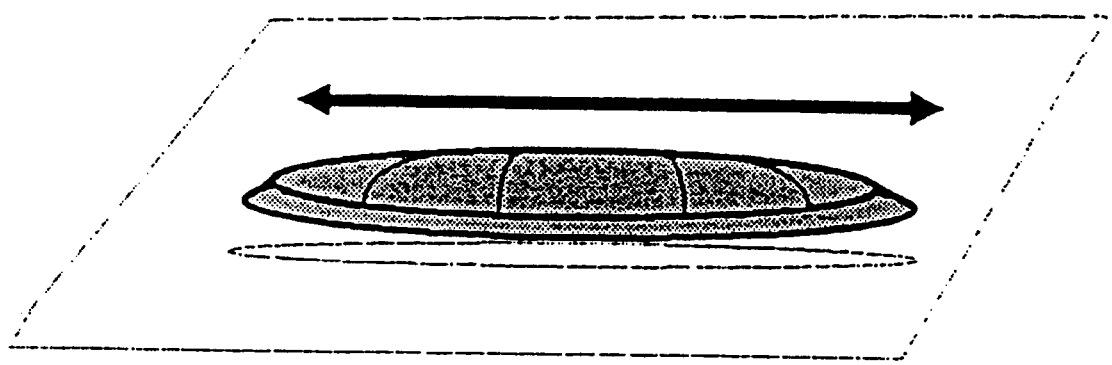
FIG. 5 shows the self-adhesive shaped body of FIG. 4 being detached from a substrate by stretching.

FIG. 5 shows that in one preferred variant embodiment the shaped body is redetachable from the substrate—that is, in particular, the skin—by stretching, in particular in the direction of the bond plane.

What is claimed is:

1. Self-adhesive shaped body which is adapted to the anatomy, has a proprioceptive effect and is intended for medical purposes, having a bond strength of from 1 N/cm to 25 N/cm, an extensibility of more than 10%, a thickness of more than 0.5 mm and a resilience of more than 50% for a tensile stress of 5 N/cm$^2$.

2. Shaped body according to claim 1, wherein to significant extents the shaped body comprises an elastic polymer selected from the group consisting of polyurethane, polyester, polyether, polyepoxide and polyolefin.

3. Shaped body according to claim 1, wherein to significant extents the shaped body comprises an elastic polymer based on a natural or synthetic rubber.

4. Shaped body according to claim 1, wherein the shaped body comprises a styrene-containing A/B or A/B/A block copolymer.

5. Shaped body according to claim 1, wherein the shaped body may be dehered by extension.

6. Shaped body according to claim 1, wherein the shaped body has a bond strength of from 1.5 to 22 N/cm.

7. Shaped body according to claim 1, wherein the shaped body is foamed and has a gas content of at least 5% by volume.

8. Shaped body according to claim 1, wherein the shaped body has at least one stippled area.

9. Shaped body according to claim 1, wherein the shaped body comprises a releasable substance having a local or systemic action.

10. Shaped body according to claim 6, wherein said bond strength is from 1.5 to 18 N/cm.

11. Shaped body according to claim 7, wherein said gas content is 10–85% by volume.

* * * * *